“(12) United States Patent
Schönherr et al.

(10) Patent No.: US 6,593,473 B1
(45) Date of Patent: Jul. 15, 2003

(54) METHOD OF PREPARING GRANULAR N-ALKYL-AMMONIUMACETONITRILE SALTS

(75) Inventors: Michael Schönherr, Frankenthal (DE); Hans-Jürgen Kinder, Speyer (DE); Klaus Mundinger, Limburgerhof (DE); Gregor Schürmann, Schwetzingen (DE)

(73) Assignee: BASF Aktiegesellschaft, Ludwigshafen (DE)

( * ) Notice: Subject to any disclaimer, the term of this patent is extended or adjusted under 35 U.S.C. 154(b) by 0 days.

(21) Appl. No.: 09/926,216
(22) PCT Filed: Mar. 17, 2000
(86) PCT No.: PCT/EP00/02378
§ 371 (c)(1), (2), (4) Date: Sep. 25, 2001
(87) PCT Pub. No.: WO00/58273
PCT Pub. Date: Oct. 5, 2000

(30) Foreign Application Priority Data

Mar. 29, 1999 (DE) .......................... 199 13 995

(51) Int. Cl.$^7$ .................... C07C 253/30; C07D 265/30
(52) U.S. Cl. .................. 544/163; 548/255; 548/336.1; 544/402; 558/430
(58) Field of Search .......................... 558/430; 544/402, 544/163; 548/255, 336.1

(56) References Cited

U.S. PATENT DOCUMENTS 4,213,924 A    7/1980    Shirley, Jr.
5,354,493 A   10/1994    Wilms
6,063,750 A    5/2000    Loeffler et al.

FOREIGN PATENT DOCUMENTS

EP   0 149 264      7/1985
WO   WO 98/08829    3/1998
WO   WO 98/23531    6/1998
WO   WO 98/23602  * 6/1998

* cited by examiner

Primary Examiner—Joseph K. McKane
Assistant Examiner—Kamal Saeed
(74) Attorney, Agent, or Firm—Oblon, Spivak, McClelland, Maier & Neustadt, P.C.

(57) ABSTRACT

Improved process for the preparation of granular N-alkylammoniumacetonitrile salts I $$R^2R^3N^+R^1\text{---}CR^4R^5\text{---}CN\ Y^- \quad (I)$$

where $R^1$ to $R^5$ are hydrogen or organic radicals, and $Y^-$ is a sulfate or hydrogensulfate anion, from an aqueous solution of the compound II $$R^2R^3N^+R^1\text{---}CR^4R^5\text{---}CN\ R^6O\text{---}SO_2\text{---}O^- \quad (II)$$

where $R^6$ is $C_1$- to $C_4$-alkyl, which comprises evaporating this aqueous solution at a temperature of from 80° C. to 250° C. and a pressure of from 10 mbar to 2 bar to give a melt, then allowing the melt to solidify, where, during or following the evaporation, customary carrier materials and/or auxiliaries can be added, and the resulting solidified compound I is converted into the desired granular form.

21 Claims, No Drawings

METHOD OF PREPARING GRANULAR N-ALKYL-AMMONIUMACETONITRILE SALTS

This application is a 371 of PCT/EP00/02378 filed Mar. 17, 2000

The present invention relates to an improved process for the preparation of granular N-alkylammoniumacetonitrile salts of the formula I

in which
- $R^1$ is a $C_1$- to $C_{24}$-alkyl group, which can be interrupted by nonadjacent oxygen atoms or can carry additional hydroxyl groups, a $C_4$- to $C_{24}$-cycloalkyl group, a $C_7$- to $C_{24}$-alkaryl group or a group of the formula —$CR^4R^5$—CN,
- $R^2$ and $R^3$ in each case independently of one another have the meaning of $R^1$ or together are a saturated 4- to 9-membered ring having at least one carbon atom and at least one other heteroatom from the group consisting of oxygen, sulfur and nitrogen,
- $R^4$ and $R^5$ in each case independently of one another are hydrogen, $C_1$- to $C_{24}$-alkyl groups, which can be interrupted by nonadjacent oxygen atoms or can additionally carry hydroxyl groups, $C_4$- to $C_{24}$-cycloalkyl groups or $C_7$- to $C_{24}$-alkaryl groups, and
- $Y^-$ is a sulfate or hydrogensulfate anion in the corresponding stoichiometric amount, from an aqueous solution of the compound of the formula II

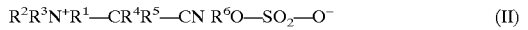

in which $R^1$ to $R^5$ are as defined above and $R^6$ is $C_1$- to $C_4$-alkyl.

N-alkylammoniumacetonitrile salts, such as N-methylmorpholiniumacetonitrile sulfate and hydrogensulfate are needed in particular as activators in the form of solids for low-temperature bleaching in detergents. WO 98/23531 describes granules of such compounds, which can additionally comprise carrier materials, for this application. For the preparation of such sulfate or hydrogensulfate granules, it is recommended to start from the methylsulfate salts.

However, known processes for the preparation of these solid N-alkylammoniumacetonitrile sulfates or hydrogensulfates are still in need of improvement. It is an object of the present invention to provide such a process which avoids the disadvantages of the prior art.

We have found that this object is achieved by the present process, which comprises evaporating the aqueous solution of the compound II at a temperature of from 80° C. to 250° C. and a pressure of from 100 mbar to 2 bar to give a melt, then allowing the melt to solidify, where, during or after the evaporation, customary carrier materials and/or auxiliaries can be added, and the resulting solidified compound I is converted into the desired granular form.

During the evaporation stage, water and also the corresponding $C_1$- to $C_4$-alcohol which becomes free upon the partial or complete thermal hydrolysis of the counterion Y are removed from the aqueous solution of the compound II.

The radical $R^1$, which has normally arisen as a result of the alkylation of the N atom, is, for example:
- a straight-chain or branched relatively long or, in particular, relatively short alkyl radical having from 1 to 24 carbon atoms, where unsaturated radicals, in particular unsaturated fatty acid radicals are also suitable, e.g. methyl, ethyl, propyl, isopropyl, butyl, isobutyl, sec-butyl, tert-butyl, pentyl, hexyl, heptyl, octyl, 2-ethylhexyl, nonyl, isononyl, decyl, undecyl, dodecyl, tridecyl, isotridecyl, myristyl, cetyl, stearyl or oleyl;
- an alkoxyalkyl radical, e.g. methoxymethyl, 2-methoxyethyl, 3-methoxypropyl, 4-methoxybutyl, 2-ethoxyethyl or 3-ethoxypropyl;
- a hydroxyalkyl radical, e.g. hydroxymethyl, 2-hydroxyethyl, 2-hydroxypropyl, 3-hydroxy-2-butyl or 4-hydroxybutyl;
- a radical constructed of repeating $C_2$- to $C_4$-alkylene oxide units such as ethylene oxide, propylene oxide or butylene oxide, which can be terminated by a hydroxyl group or an alkoxy group, e.g. $(C_2H_4O)_n$—H or —$(C_2H_4O)_n$—$R^7$, —$(C_3H_6O)_m$—H or —$(C_3H_6O)_m$—$R^7$, —$(C_4H_8O)_k$—H or —$(C_4H_8O)_k$—$R^7$ n=2 to 11, m=2 to 7, k=2 to 5, $R^7$=methyl or ethyl);
- a cycloalkyl group such as cyclopentyl, cyclohexyl or cycloheptyl;
- an aralkyl group such as benzyl, 2-phenylethyl, 3-phenylpropyl or 4-phenylbutyl;
- a group of the formula —$CH_2$—CN, —$CH(CH_3)$—CN or —$C(CH_3)_2CN$.

Preferred meanings for $R^1$ are a $C_1$- to $C_4$-alkyl group or a benzyl radical.

The meanings for the radicals $R^4$ and $R^5$ are in principle the same as for $R^1$ (with the exception of —$CR^4R^5$—CN), and they can additionally also be hydrogen. Preferred meanings for $R^4$ and $R^5$ are hydrogen, methyl and ethyl, and in particular both are hydrogen.

In a preferred embodiment, $R^1$ is a $C_1$- to $C_4$-alkyl group or a benzyl radical, and $R^4$ and $R^5$ are both hydrogen at the same time.

The meanings for the radicals $R^2$ and $R^3$ are principally the same as for $R^1$ for open-chain alicyclic structures. Additionally, $R^2$ and $R^3$ can, together with the ammonium N atom, be a saturated heterocyclic ring. Suitable in particular in this connection are those which, apart from the ammonium N atom, contain no, one or two further heteroatoms from the group consisting of oxygen, sulfur and nitrogen, especially from the group consisting of oxygen and nitrogen. Preferred ring sizes are five-, six- and seven-membered rings. Examples of heterocyclic systems which are suitable for this purpose are imidazolidine, 1,2,3-triazolidine and piperazine.

Particular preference is given to systems in which $R^2$ and $R^3$ together are a saturated six-membered ring having 5 carbon atoms or having 4 carbon atoms and one oxygen or one nitrogen atom. These are in particular piperidine and morpholine systems.

The radical $R^6$ is, for example, methyl, ethyl, propyl, isopropyl, butyl, isobutyl, sec-butyl or tert-butyl, preferably methyl.

According to the process of the invention, very particular preference is given to preparing granular N-methylmorpholiniumacetonitrile hydrogensulfate from an aqueous solution of N-methylmorpholiniumacetonitrile methylsulfate.

Depending on the pressure, the evaporation is carried out at temperatures of from 80° C. to 250° C., preferably from 90° C. to 200° C., in particular at from 100° C. to 160° C. In the preferred pressure range, temperatures from 100° C. to 160° C. are particularly favorable because then adequate removal of water and alcohol takes place and the decomposition of the acetonitrile I to the corresponding amide stage is still negligibly slight.

The evaporation is carried out at a pressure of from 10 mbar to 2 bar, preferably from 100 mbar to 1.1 bar, in particular at from 250 to 960 mbar. Preference is given to evaporation under a slight vacuum since under these conditions volatile secondary components can be driven off more easily.

The evaporation step is preferably carried out in a continuous procedure, for example in a Sambay evaporator, a thin-film contact dryer, a falling-film evaporator or a tube-bundle heat exchanger. The evaporation can, however, also be carried out discontinuously, i.e. in a batch process, e.g. in a reactor.

The required residence time for the evaporation step is dependent on the temperature chosen and the pressure chosen and is generally in the range from a few minutes to several hours. A typical range is from 2 minutes to 15 hours, in particular from 5 minutes to 5 hours. In the preferred temperature and pressure range, a residence time of from 5 to 15 minutes is particularly favorable. Residence times which are too long can trigger the decomposition of the product. The residence time distribution should be narrow, in the case of a continuous procedure, the plugflow pattern should be strived for in order to avoid the formation of by products and decomposition products.

In a particularly preferred embodiment, the evaporation is carried out continuously with a residence time of from 5 to 15 minutes.

Leaving the evaporation stage are the product melt and vapors in the form of predominantly water and alcohol vapor. In the process according to the invention, the significant reduction in the input of energy can be achieved by using the condensation of the vapors produced during the evaporation to preheat the aqueous solution of the compound II. As regards apparatus, tube-bundle or plate-type heat exchangers can, for example, be used for this purpose.

The melts produced in this way usually have a water content of at most 30% by weight, in particular of at most 20% by weight, especially from 1 to 10% by weight. The proportion of the sulfate or hydrogensulfate salt I in the melt is usually at least 50% by weight, in particular at least 70% by weight, especially at least 80% by weight. The aqueous solution of the compound II used as starting material usually has a solids content of from 5 to 80% by weight, in particular from 10 to 75% by weight, especially from 25 to 65% by weight.

Prior to solidification, it is possible to mix the melt with customary carrier materials and/or auxiliaries. These carrier materials can be water-soluble or water-insoluble, depending on the field of application. Examples of such carrier materials, which are added during or after the evaporation, are sodium sulfate, silicas and zeolites. It is also possible to add two or more of said carrier materials, i.e. mixtures thereof. As well as carrier materials, functional auxiliaries such as surfactants can also be added to the melt.

The mixing with the carrier materials or auxiliaries can either be carried out in any separate apparatus, e.g. in a stirred vessel, or in a continuous mixer. The mixture can then be solidified by contact cooling, e.g. on a cooling roll, on a cooling belt or in a cooling mixer, or by convective cooling, e.g. in a prilling tower or in spray granulation equipment. It is, however, also possible to carry out the mixing and solidification of the melt in the same apparatus, e.g. in an extruder, kneader reactor or cooling mixer.

The cooling process can be carried out at superatmospheric pressure, atmospheric pressure or under reduced pressure. In principle, it is possible to operate here within the same pressure ranges as for the evaporation step. Preference is given in the case of the cooling process to carrying out the procedure under atmospheric pressure or, as in the case for the evaporation step, under slightly reduced pressure as a result of suction.

The cooling temperatures can be in the range from the solidification temperature of the melt to very negative temperatures, as, for example, is the case during cooling with liquid nitrogen (−196° C.). Preference is given to cooling temperatures in the range from −50° C. to +30° C., in particular from −20° C. to +20° C.

The required residence time of the solidification process depends on the crystallization properties of the substance mixture and is generally in the range from a few minutes (e.g. 5 minutes) to one hour. Intimate thorough mixing, as occurs for example in extruders or kneader reactors, can considerably shorten the required crystallization time in many cases.

According to the solidification process, the product, which contains the salt I in addition to any remaining starting material II and optionally carrier materials and/or auxiliaries, is usually in the form of a solid with a broad particle size distribution and thus still does not satisfy, for example, the requirements for detergent granules. The desired granular form with respect to the particle size can be obtained by suitable screening and/or grinding steps with customary processing equipment. Customary particle sizes are from 100 to 5000 micrometers, in particular from 300 to 2000 micrometers.

The process according to the invention has a number of advantages. For example, it permits conversion with a low by product level and the reduction of volatile secondary components. The preferred continuous procedure results in high yields. Because the hold-up in the plant is short, the continuous procedure is advantageous for reasons of safety. The fact that it is possible to recover heat means that the process is energetically favorable. It is possible to use a very wide variety of carrier materials and auxiliaries in the granulation process. Furthermore, the particle size distribution in the granulation process can be readily controlled.

EXAMPLE

An 80 liter glass vessel was charged with 60 liters of a 65% by weight aqueous solution of N-methylmorpholiniumacetonitrile methylsulfate. The solution was heated to 110° C. and evaporated at a pressure of 600 mbar over a period of 3 hours. The melt, which had a content of N-methylmorpholiniumacetonitrile hydrogensulfate of about 80% by weight (the remainder consisted essentially of inorganic salts and water), was then introduced onto 20 kg of a standard commercial silica in a 160 liter Lödige mixer, and the mixture was solidified. The solidified mixture was then screened to a particle size of from 350 to 1600 micrometers. The coarse material greater than 1600 micrometers was ground and then rescreened. This gave granules with a content of about 60% by weight of N-methylmorpholiniumacetonitrile hydrogensulfate.

We claim:

1. A process for the preparation of granular N-alkylammoniumacetonitrile salts of the formula I $$R^2R^3N^+R^1\text{—}CR^4R^5\text{—}CN\ Y^- \qquad (I)$$

wherein
$R^1$ is a $C_1$- to $C_{24}$-alkyl group, which can be interrupted by nonadjacent oxygen atoms or can carry additional hydroxyl groups, a $C_4$- to $C_{24}$-cycloalkyl group, a $C_7$- to $C_{24}$-alkaryl group or a group of the formula —$CR^4R^5$—CN, R² and R³ in each case independently of one another have the meaning of R¹ or together are a saturated 4- to 9-membered ring having at least one carbon atom and at least one other heteroatom from the group consisting of oxygen, sulfur and nitrogen, R⁴ and R⁵ in each case independently of one another are hydrogen, $C_1$- to $C_{24}$-alkyl groups, which can be interrupted by nonadjacent oxygen atoms or can additionally carry hydroxyl groups, $C_4$- to $C_{24}$-cycloalkyl groups or $C_7$- to $C_{24}$-alkaryl groups, and Y⁻ is a sulfate or hydrogensulfate anion in the corresponding stoichiometric amount, from an aqueous solution of the compound of the formula II

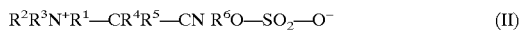
(II)

wherein R¹ to R⁵ are as defined above and R⁶ is $C_1$- to $C_4$-alkyl, comprising:

(a) evaporating said aqueous solution at a temperature ranging from 80° C. to 250° C. and a pressure ranging from 10 mbar to 2 bar to give a melt having a residual water content of at most 20% by weight, (b) allowing the melt to solidify, where, during or following the evaporation, customary carrier materials and/or auxiliaries can be added, and (c) converting the solidified compound I obtained from (b) into the desired granular form, wherein hydrolysis of the counterion R⁶O—SO₂O⁻ to Y⁻ takes place thermally and without the addition of an acid.

2. A process for the preparation of granular N-alkylammoniumacetonitrile salts I as in claim 1, in which R¹ is a $C_1$- to $C_4$-alkyl group or a benzyl radical, and R⁴ and R⁵ are hydrogen.

3. The process for the preparation of granular N-alkylammoniumacetonitrile salts I as in claim 1, in which R² and R³ together are a saturated six-membered heterocyclic ring having a nitrogen atom and zero, one, or two additional heteroatoms selected from the group consisting of oxygen, sulfur, and nitrogen.

4. A process for the preparation of granular N-methylmorpholiniumacetonitrile hydrogen sulfate from an aqueous solution of N-methylmorpholiniumacetonitrile methylsulfate as in claim 1.

5. A process for the preparation of granular N-alkylammoniumacetonitrile salts I as in claim 1, wherein the temperature of evaporation is carried out at a temperature of 100° to 160° C.

6. A process for the preparation of granular N-alkylammoniumacetonitrile salts I as in claim 1, wherein the evaporation is carried out at a pressure of from 250 to 900 mbar.

7. A process for the preparation of granular N-alkylammoniumacetonitrile salts I as in claim 1, wherein the evaporation is carried out continuously with a residence time of from 5 to 15 minutes.

8. A process for the preparation of granular N-alkylammoniumacetonitrile salts I as in claim 1, wherein the heat of condensation of the vapors produced during evaporation is used to prewarm the aqueous solution of the compound II.

9. The process for the preparation of granular N-alkylammoniumacetonitrile salts I as in claim 1, wherein the evaporation is carried out until the residual water content ranges from 1 to 10% by weight.

10. A process for the preparation of granular N-alkylammoniumacetonitrile salts I as in claim 1, wherein, during or following the evaporation, one or more carrier materials from the group consisting of sodium sulfate, silicas and zeolites are added.

11. The process for the preparation of granular N-alkylammoniumacetonitrile salts I as in claim 1, wherein said saturated 4- to 9-membered ring is selected from the group consisting of imidazolidine, 1,2,3-triazolidine, and piperazine.

12. The process for the preparation of granular N-alkylammoniumacetonitrile salts I as in claim 1, wherein the evaporation is carried out continuously with a residence time of 2 minutes to 15 hours.

13. The process for the preparation of granular N-alkylammoniumacetonitrile salts I as in claim 1, wherein the evaporation is carried out continuously with a residence time of 5 minutes to 5 hours.

14. The process for the preparation of granular N-alkylammoniumacetonitrile salts I as in claim 1, wherein the temperature during evaporation ranges from 90 to 200° C.

15. The process for the preparation of granular N-alkylammoniumacetonitrile salts I as in claim 1, wherein the pressure during evaporation ranges from 100 mbar to 1.1 bar.

16. The process for the preparation of granular N-alkylammoniumacetonitrile salts I as in claim 1, wherein the proportion of the sulfate or hydrogensulfate salt I in the melt is at least 50% by weight.

17. The process for the preparation of granular N-alkylammoniumacetonitrile salts I as in claim 1, wherein the proportion of the sulfate or hydrogensulfate salt I in the melt is at least 70% by weight.

18. The process for the preparation of granular N-alkylammoniumacetonitrile salts I as in claim 1, wherein the proportion of the sulfate or hydrogensulfate salt I in the melt is at least 80% by weight.

19. The process for the preparation of granular N-alkylammoniumacetonitrile salts I as in claim 1, wherein the aqueous solution of compound II used as the starting material has a solid content ranging from 5 to 80% by weight.

20. The process for the preparation of granular N-alkylammoniumacetonitrile salts I as in claim 1, wherein the aqueous solution of compound II used as the starting material has a solid content ranging from 10 to 75% by weight.

21. The process for the preparation of granular N-alkylammoniumacetonitrile salts I as in claim 1, wherein the aqueous solution of compound II used as the starting material has a solid content ranging from 25 to 65% by weight.

* * * * *